United States Patent [19]

Battista

[11] 4,264,493
[45] Apr. 28, 1981

[54] NATURAL PROTEIN POLYMER HYDROGELS

[76] Inventor: Orlando A. Battista, 3725 Fox Hollow Rd., Ft. Worth, Tex. 76109

[21] Appl. No.: 74,014

[22] Filed: Sep. 14, 1979

Related U.S. Application Data

[63] Continuation-in-part of Ser. No. 952,303, Oct. 18, 1978, abandoned.

[51] Int. Cl.$^3$ .................... C07G 7/00; C08H 1/00; C08H 1/06; C09H 9/00
[52] U.S. Cl. .......................... 260/117; 3/1.9; 106/125; 106/135; 106/154 R; 106/161; 128/92 C; 260/112R; 260/123.5; 260/123.7; 264/1.1; 351/160 H; 351/160 R; 351/161; 351/162; 424/177; 424/359; 424/360
[58] Field of Search ............... 260/112 R, 117, 123.5, 260/123.7; 264/1; 106/161, 135

[56] References Cited

U.S. PATENT DOCUMENTS

| | | | |
|---|---|---|---|
| 3,099,562 | 7/1963 | Rogers | 260/112 X |
| 3,157,524 | 11/1964 | Artandi | 106/122 |
| 3,393,080 | 7/1968 | Erdi et al. | 260/123.7 X |
| 3,443,261 | 5/1969 | Battista et al. | 260/123.7 UX |
| 3,607,860 | 9/1971 | Yamato et al. | 260/123.5 |
| 3,628,974 | 12/1971 | Battista | 260/123.7 X |
| 3,632,361 | 1/1972 | Battista | 260/123.7 X |
| 3,649,347 | 3/1972 | Battista | 260/123.7 X |
| 3,691,281 | 9/1972 | Battista | 260/123.7 |
| 3,767,437 | 10/1973 | Cruz | 106/161 |
| 3,823,212 | 7/1974 | Chvapil | 260/123.7 X |
| 3,965,063 | 6/1976 | Holcombe | 264/1 X |
| 4,096,870 | 6/1978 | Manfuso | 264/1 X |
| 4,121,885 | 10/1978 | Erickson et al. | 264/1 X |
| 4,123,408 | 10/1978 | Gordon | 264/1 X |

*Primary Examiner*—Howard E. Schain
*Attorney, Agent, or Firm*—George F. Mueller

[57] ABSTRACT

Natural protein hydrogel structures formed from natural proteins having molecular weights not exceeding 100,000 by dissolving the protein in an aqueous acidic solution, crosslinking the protein, and air drying to a moisture content not exceeding 10 percent. The air dried structure may or may not be bleached with an aqueous solution of an oxidizing agent and thoroughly washed with water. The washed structure is dehydrated by treatment with a water-miscible organic solvent, washed with water, and redried to a moisture content of not more than 10 percent. The structures may be in the form of soft contact lenses, films, fibers, and prosthetics.

18 Claims, No Drawings

NATURAL PROTEIN POLYMER HYDROGELS

This application is a continuation-in-part of application Ser. No. 952, 303 filed Oct. 18, 1978, now abandoned.

This invention relates to new hydrogel forms of natural animal and vegetable proteins which have superior properties compared with present known forms of the same materials. It more specifically relates to such compositions as soft contact lenses (disposable, fugitive, and dressing forms), and cosmetic, pharmaceutical, and surgical preparations containing these new forms of natural animal and vegetable proteins when used in contact with aqueous liquids. The invention also relates to methods of producing superior and more widely useful products from such natural proteins than has been heretofore possible.

By natural hydrogel (hydrocolloidal) animal or vegetable protein polymers is meant throughout the specification and claims a crosslinked protein polymer of natural origin having an average molecular weight of about 100,000 or less, capable of being swollen by water over a wide range of water contents ranging from as low as 30 percent to 1000 percent and higher while possessing useful rheological control properties for specific end product uses.

Specifically, one object of this invention is to provide soft contact lenses capable of being colored completely or at least partly if desired using effective protein dyes, lenses that will correct optical defects of the wearer's eye.

Another object of this invention is to produce contact lenses that may be worn continuously until they become cloudy—and can be thrown away (disposable), and replaced by a fresh lens or a pair of lenses.

Still another object of the invention is to control the properties of contact lenses—using the same raw materials—so that such lenses may have their properties so engineered in advance that they may be used as corneal dressings, fugitive lenses, or in the form of rigid rheologically-tailored hydrogels, capable of serving as a replacement for vitreous fluids.

Still another object of this invention is to control the composition and chemistry of the natural protein hydrogels to provide burn and wound dressings having superior properties in the wet state.

A further object of the invention is to adapt this new technology to produce novel fibers for textile and medical uses.

A still further object of the invention is to provide a hydrogel base from which bone-like structures, arteries, and similar prostheses possessing outstanding properties in an aqueous fluid saturated state never before available.

The art has long worked with low molecular weight proteins (such as animal gelatins) and vegetable proteins (such as soybean proteins)—using them with and without varying degrees and types of crosslinking. However, great limitations, especially in wet physical properties, of such prior products limited their use, especially in the structural forms described by the present invention. For example, prior art has clearly concluded that gelatin or agar never were found suitable to produce contact lenses (Soft Contact Lens, by Montague Ruben, John Wiley & Sons, p. 25, 1978).

The present invention provides new forms of treated protein polymers that possess unique physical properties, especially in the wet state, properties that are critically dependent upon the specific sequence of controlling pH, crosslinking agent concentration, and most critically on drying the structures to critical levels in accordance with specific stepwise chemical and solvent dehydration sequences. Products prepared using previously reported conditions of crosslinking and drying did not possess the outstanding wet physical integrity of products prepared in accordance with the findings of this invention. They were deficient in physical integrity to sustain the performance in the wet state provided by the products of the present invention.

In producing my products, it is essential to begin with natural protein raw materials that form clear solutions in water at concentrations up to 30 percent or higher. Ordinary household unflavored gelatin is a typical starting natural animal protein as one starting raw material for this invention and edible soybean protein is a typical starting vegetable protein example.

Depending on the desired end-product form, I have found that controlling such variables as pH, crosslinking agent, temperature, solids concentration, and solvent dehydration sequences are critical variables. A further critical variable is to air dry at temperatures not exceeding about 35° C. to a moisture content in the dried form of not more than 10 percent, preferably 7 percent or less. I have found that if these critical steps are not carried out, e.g. if the products are heated to 40° C. or higher at any time prior to the final air drying to not more than 10 percent moisture and do not receive appropriate organic solvent dehydration treatments, unsatisfactory water instability in the final products results. Instead of possessing extremely pliable, bendable, and good physical integrity including superior tear strength properties in the wet state, products that are dried in any manner before initially being air dried to not more than 10 percent moisture, and preferably below 7 percent moisture, in sequence with organic solvent dehydration treatments give products having a cheese texture, extremely brittle and friable physcial state when saturated with water. Of course, loss of wet physical integrity such as above described (and clearly characteristic of the prior art) makes the resulting products essentially useless for the products produced by this invention: e.g. soft contact lenses, ophthalmological dressings, artificial corneas, vitreous fluid, novel protein fibers for textile and surgical uses, prostheses such as artificial cartilage and artificial bone, capsules, sutures, burn and wound dressings, etc. The importance of this invention lies in making possible a wide range of products having such a wide line of useful properties from inexpensive and abundant relatively low molecular weight natural protein raw materials.

Although Formalin (37% Formaldehyde solution) is the crosslinking agent used in illustrating the examples, other suitable crosslinking agents may be used, such as glyoxal, glutaraldehyde, ethylene glycoldimethacrylate, diethylene glycoldimethacrylate or methylene-bismethacrylamide, together with an aqueous solution, for example, a 4% by weight solution of ammonium persulphate or potassium persulphate, or another peroxidic initiator or polymerisation and an activator, such as for example 2-dimethylenaminomethyl-acetate, or a p-toluene sulphonic acids. A small amount of cuprous salts or bivalent iron salts may be added.

The products of the present invention are prepared from solutions of the natural protein containing from about 0.5 percent to about 15 percent, by weight, preferably from 0.5 percent to 10 percent, of the protein or mixtures of the proteins. The solution is heated to 60°±5° C. so as to aid in dissolving the protein and produce a clear solution. Following the dissolution of the protein, the pH of the solution is adjusted to about pH 3.5 to about pH 5.5 and thereby form an aqueous acidic solution of the protein. While maintaining the acidic solution within this temperature range, the crosslinking agent is added to and incorporated in the solution with vigorous mixing. Commercial Formalin containing 37% formaldehyde is particularly convenient and satisfactory as the crosslinking agent. Formalin is added to the solution in an amount sufficient to provide from about 0.5 percent to about 15 percent, preferably from 0.5 percent to 10 percent formaldehyde, based upon the weight of the protein. Equivalent amounts of other crosslinking agents may be substituted for Formalin.

The solution is cast or formed into a desired dimensional configuration or structure followed by air drying at temperatures not exceeding 35° C. to a moisture content of not more than 10 percent, preferably less than 7 percent. In instances where a clear, water white product is desired, the dried structure is bleached by the use of an oxidizing agent, such as, for example, hydrogen peroxide, sodium hypochlorite, and the like. Where the characteristic tan color of low molecular weight proteins is not objectionable, this treatment may be omitted. The bleached or unbleached structure is thoroughly washed with water followed by a dehydration treatment by immersion in a water-miscible organic solvent, such as, for example, ethanol, denatured ethanol, isopropanol, acetone, and the like. After the organic solvent treatment, the structure is thoroughly washed with water and air dried at temperatures not exceeding 35° C. to reduce the moisture content to not more than 10 percent, preferably less than 7 percent.

Because the base raw material is proteinaceous, products made in accordance with this invention lend themselves to being permanently dyed in single or multiple colored forms and designs using dyeing procedures commonly applied to polymer materials containing NH, $NH_2$, and COOH groups. Accordingly, any desired color either for functional or cosmetic purposes may be imparted to these products by the addition of suitable dyes or pigments.

A few of the preferred examples of carrying out the invention are given below.

EXAMPLE 1

A 400 ml clean gel mixture comprising 400 ml of a 10 percent gelatin solution (approximately 50,000 molecular weight and a bloom of 225) was heated to 60° C. To this clear mixture is added with smooth, steady stirring 4 drops of 10N HCl bringing the pH to 4.30. Immediately thereafter, 8 ml of Formalin, approximately 7.5 percent formaldehyde based on the gelatin, is added to the mixture with vigorous mixing, maintaining the temperature at 60°±5° C.

The initial casting of the natural hydrogel, preconditioned as above, to produce a water-stable product must be carried out promptly after the addition of the crosslinking agent. The casting may be done either by stationary air drying in a mold or by spin casting and drying in a mold.

Disposable Soft Contact Lens

From a burette or measuring pipette, 4 drops of the above mixture are carefully added to standard polymethacrylate (11 mm) diameter molds under ambient temperature conditions. The thickness of the contact lens—as well as its refractory properties—are predetermined both by concavity specifications of these molds and the number of drops added to them at a given concentration level, respectively. The hydrogel is allowed to dry slowly at about 25° C. (R.T.) for at least 24 hours, during which the crosslinking reaction proceeds essentially to completion.

At the end of this drying cycle, the lenses still in their molds are given a further drying in an air circulating oven for a minimum of 4 hours at 30°-35° C. maximum to insure that the moisture content at this point of production is reduced to not more than 10 percent, preferably less than 7 percent.

The lenses are now easily removed from the molds and immediately immersed in a dilute aqueous solution of standard household hydrogen peroxide (3% by volume) for a minimum of 1 hour at R.T. (25° C.). This step is especially effective in substantially removing the natural tan or light brown coloration characteristic of relatively low molecular weight, natural proteins—whether crosslinked or not.

The lenses now receive a vigorous and thorough washing using distilled water, preferably, to insure removal of all residual minute amounts of crosslinking reagent and any residual hydrogen peroxide.

After this thorough washing treatment the water-swollen lenses are added to commercial (either undenatured or denatured) ethyl alcohol (95% by volume), and allowed to remain immersed therein for a minimum of two hours.

At the end of the ethyl alcohol dehydration soaking treatment, the lenses are once again washed thoroughly with distilled water to remove all traces of residual ethyl alcohol and related denaturation components if denatured ethyl alcohol is used. Repeated extensive washings in distilled water, preferably, is important at this step.

The thoroughly rewashed clear lenses are now slowly air dried once again using the precise sequence described above—namely—air dired for 25 hours at about R.T. (25° C.), followed by a minimum of 4 hours in an air circulating oven at 30°-35° C. maximum, until the residual moisture content is reduced to not more than 10 percent, preferably below 7 percent. If desired, the final water-washed lenses may be dried in their respective molds in which they were originally cast, although this is purely an option. Sterilization, if desired, is effected by dry heating at temperatures up to 120° C.

This completes the manufacturing sequence (subject to subsequent inspection, edge-bevelling if desired, packaging, and sterilization, etc.) to obtain water-white soft contact lenses having superior physical properties and gaseous transmission properties both in the wet and dry states, respectively. Among these advantages are almost immediate water hydration (2-3 minutes versus 1-2 hours or longer for conventional HEMA-type synthetic polymer soft contact lenses) along with high levels of oxygen gas permeability.

EXAMPLE 2

A 400 ml clear gel mixture comprising 300 ml of a 10 percent gelatin solution and 100 ml of a 1 percent partially hydrolyzed bovine edible collagen (molecular weight of about 100,000) is heated to 60° C. To this mixture is added with smooth, steady stirring 4 drops of 10N HCl, bringing the pH to 4.65. Immediately thereafter, 8 ml of Formalin, approximately 9.5 percent formaldehyde based on the protein, is added to the mixture with vigorous mixing, maintaining the temperature at 60° C.±5° C.

The initial casting of the natural hydrogel preconditioned as above to produce a water-stable product must be carried out promptly after the addition of the crosslinking agent.

Conventional Soft Contact Lenses

From a burette or measuring pipette, 4 drops of the above mixture are carefully added to standard polymethacrylate (11 mm) diameter molds under ambient temperature conditions. The thickness of the contact lens—as well as its refractory properties are predetermined both by the concavity specifications of these molds and the number of drops added to them at a given concentration level, respectively.

The air drying, bleaching, washing, dehydration, washing, and final air drying steps are identical to those described in detail in Example 1.

The resulting water-white contact lenses are suitable for continuous wear as soft contact lenses. They lend themselves to economical mass production as that they may also be used as disposable lenses—capable of being discarded once they develop excessive clouding due to coating deposits, etc. If so desired, these contact lenses may provide a route to the elimination of repeated use of costly cleaning solutions and the infection hazards related to repeated removal handling of the lenses for daily cleaning.

EXAMPLE 3

A 400 ml. clean gel mixture comprising 400 ml of a 10 percent gelatin solution (approximately 50,000 molecular weight and a bloom of 225) was heated to 60° C. To this clear mixture is added with smooth, steady stirring 4 drops of 10N HCl, bringing the pH to 4.76. Immediately thereafter, 80 drops (4 ml) of Formalin, approximately 3.7% formaldehyde based on the gelatin, is added to the mixture with vigorous mixing, maintaining the temperature at 60° C.±5° C.

The initial casting of the natural hydrogel preconditioned as above to produce a water-soluble product must be carried out promptly after the addition of the crosslinking agent.

Fugitive Soft Contact Lens Dressings

From a burette or measuring pipette, 4 drops of the above mixture are carefully added to special 14–15 mm diameter glass molds under ambient temperature conditions. The thickness of the contact lens—as well as its refractory properties are predetermined both by the concavity specifications of these molds and the number of drops added to them at a given concentration level, respectively.

The air drying, bleaching, washing, dehydration, washing, and final air drying steps are identical to those described in detail in Example 1.

This completes the manufacturing sequence (subject to subsequent inspection, edge-bevelling if desired, packaging, and sterilization, etc.) to obtain water-white soft contact lenses whose properties in the wet state make them ideal for use as fugitive dressings for ophthalmological use. For example, lenses prepared in this way possess low wet abrasion properties; when placed in the eye along with medication, the movement of the eyelids over the dressing progressively erodes the dressing so that it is washed away over a period of 10–16 hours by the tear flow. Furthermore, such hydrogel lenses or film strips when saturated with glaucoma treatment drugs such as pilocarpine or timoptic (formulated from timolol maleate) proffer use in lieu of high viscosity drops when mechanically dispensed into the eye.

EXAMPLE 4

A 400 ml clean gel mixture comprising 200 ml of a 10 percent gelatin solution (approximately 50,000 molecular weight and a bloom of 275) and 200 ml of a 2 percent partially hydrolyzed bovine edible collagen (molecular weight of about 100,000) is heated to 60° C. To this mixture is added with smooth, steady stirring 4 drops of 10N HCl, bringing the pH to 5.10. Immediately thereafter, 8 ml (160 drops) of Formalin, approximately 12.3% formaldehyde based on the protein, is added to the mixture with vigorous mixing, maintaining the temperature at 60° C.±5° C.

The initial casting of the natural hydrogel preconditioned to produce a water-stable product must be carried out promptly after the addition of the crosslinking agent, e.g. before the crosslinking reaction proceeds irreversibly to a solid, non-pourable gel.

Durable Ophthalmological Films and Corneal Transplants

From a burette or measuring pipette, 3 drops of the above mixture are carefully added to standard polymethacrylate (11 mm) diameter molds under ambient temperature conditions. The thickness of the contact lens—as well as its refractory properties—are predetermined both by the concavity specifications of these molds and the number of drops added to them at a given concentration level, respectively.

The air drying, bleaching, washing, dehydration, washing, and final air drying steps are identical to those described in detail in Example 1.

EXAMPLE 5

A 400 ml clean gel mixture comprising 400 ml of a 10 percent gelatin solution (approximately 50,000 molecular weight and a bloom of 225) was heated to 60° C. To this clear mixture is added with smooth, steady stirring 4 drops of 10N HCl, bringing the pH to 4.35. Immediately thereafter, 40 drops (2 ml) of Formalin, approximately 1.85% formaldehyde based on the gelatin, are added to the mixture with vigorous mixing, maintaining the temperature at 60° C.±5° C.

Viscosity-Control Hydrogels

This product is allowed to stand at room temperature (25° C.) for at least 15 minutes with continuous stirring to insure maximum homogenization of the crosslinking process.

The hydrogel is then dried preferably by flash spray drying, thereby converting it into a find particulate form. Or the hydrogel may be spread out in trays to be slowly air dried.

No matter what drying procedure is used, it is necessary that the moisture content be reduced at the drying step, using maximum temperatures at atmospheric pressure of 30°–35° C., to a residual moisture content of not more than 10 percent, preferably less than 7 percent.

The dry natural protein polymer hydrogel particles are next immersed in a dilute aqueous solution of standard household hydrogen peroxide (3% by volume) for a minimum of 1 hour at R.T. (25° C.). This step is especially effective in substantially removing the natural tan or light brown coloration characteristic of relatively low molecular weight, natural proteins—whether crosslinked or not.

The swollen hydrogel particles now receive a vigorous and thorough washing using distilled water, preferably, to insure removal of all residual minute amounts of crosslinking reagent and any residual hydrogen peroxide.

After the above thorough washing treatment, the water-swollen hydrogel particles are added to commercial (either undenatured or denatured) ethyl alcohol (95% by volume), and allowed to remain immersed therein for a minimum of two hours.

At the end of the ethyl alcohol dehydration soaking treatment, the hydrogel particles are once again washed thoroughly with distilled water to remove all traces of residual ethyl alcohol and related denaturation components if denatured ethyl alcohol is used. Repeated extensive washings in distilled water, preferably, is important at this step.

The thoroughly rewashed clear, highly swollen hydrogel clusters are now slowly air dried once again using the precise drying sequence described above—namely—either spray dried or air dried until the residual moisture content does not exceed 10 percent, preferably below 7 percent.

The resulting product is especially suitable when swollen in aqueous ophthalmological solutions (e.g. pilocarpine hydrochloride solutions for treating glaucoma) for controlling the viscosity and flow properties. More importantly, the high swollen network internal structure of the hydrogel particles provides a means of prolonging the action of drug components of which they are an ingredient.

EXAMPLE 6

A 800 ml clear gel mixture comprising 600 ml of a 10 percent gelatin solution and 200 ml of a 1 percent partially hydrolyzed bovine edible collagen (molecular weight of about 100,000) is heated to 60° C. To this mixture is added with smooth, steady stirring 10 drops of 10N HCl, bringing the pH to 4.80. Immediately thereafter 18 ml of Formalin, approximately 10.7% formaldehyde based on the protein, is added to the mixture with vigorous mixing, maintaining the temperature at 60° C.±5° C.

Films, Burns and Wounds Dressings

Immediately after thoroughly mixing the above composition, it is deaerated in a vacuum desiccator at 28–29 inches of vacuum to help deaerate bubbles. The mixture is next cast into flat Pyrex dishes the dimensions of which are chosen to reflect the final dimensions desired for the film. For example, a circular film or dressing may be made by using a Petri dish, a rectangular film by using a rectangular glass dish.

The hydrogel is allowed to dry slowly at about 20° C. (R.T.) for at least 24 hours, during which the crosslinking reaction proceeds essentially to completion. Depending on the thickness of the film desired, slow air drying may continue for a period of a week or more until all of the hydrogel has been dried to not more than 10 percent moisture, preferably less than 7 percent residual moisture. In order to reduce the drying time, after 24 hours the mold containing the shaped structure may be further dried in an air circulating oven.

Should it be desired to produce a film which is fabric laminated within or fabric laminated to such hydrogel products, the fine mesh fabric is placed smoothly in the casting chamber before the fluid hydrogel is cast.

Subsequent handling of such cast films follows the sequence of treatments involving whitening with an oxidizing ($H_2O_2$) agent, followed by a treatment using organic solvent dehydration steps, etc., all as described for producing contact lenses having unique physical and chemical properties (Example 1).

EXAMPLE 7

Tubes, Arteries, and Other Structural Forms

Using the same formulation described in Example 6, the deaerated hydrogel is poured into a concentric mold in order to cast a tube (or artery), with or without a fabric matrix within the mold.

The crosslinking reaction is allowed to proceed at R.T. (25° C.) and 58 percent R.H. for at least 24 hours and to bring the moisture content to not more than 10 percent. The solid hydrogel is slipped out of its concentric mold to form a tubular structure suitable for use as an artery-like prosthesis.

The tubes are then subjected to bleaching, washing, dehydration, washing, and final air drying steps identical to those described in detail in Example 1.

EXAMPLE 8

Bone-Like Prostheses

The starting raw material for producing both cancellous-like and cortical-like prosthesis from the stabilized natural protein polymer hydrogels of this invention is identical to or closely similar to the formulation described on Example 6. One of the major differences involves the use of phosphoric acid in preference to hydrochloric acid to adjust the acidity of the hydrogel prior to the addition of the crosslinking reagent.

The initial water-soluble non-crystalline natural protein solution has intimately dispersed within it calcium phosphate particles or crystals with or without inclusion of other ions such as are found in naturally occurring bone and cartilage. The product consists primarily of an intimate and homogenous physical mixture of the various ingredients and various ions may be included to increase the hardness of the product prior to the addition of the protein crosslinking agents described in prior examples.

The calcium phosphate may be formed by mixing solutions of a soluble calcium salt, such as calcium acetate, and of a soluble phosphate, such as sodium phosphate. In the event other salts and/or ions are to be included, such as the fluoride or carbonate ions, soluble salts, such as calcium fluoride or sodium carbonate, may be incorporated in the salt solutions during the formation of the calcium phosphate. The precise structure of the calcium phosphate compounds formed are complex and the term "calcium phosphate" is used to include dicalcium phosphate, tricalcium phosphate, octacalcium phosphate, hydroxyapatite, carbonate-apatite, chlorapatite, fluorapatite, and mixtures thereof.

A modification of Example 6 found to be desirable in producing extremely porous, cancellous-type prostheses is the replacement of water as the protein solvent with a dilute aqueous solution of hydrogen peroxide, for example, a 1 percent by volume aqueous solution. Following dissolution of the protein in the dilute solution of hydrogen peroxide, a sufficient amount of a 25 percent (by weight) aqueous slurry of calcium phosphate was incorporated into the protein solution to provide approximately equal amounts of protein and calcium phosphate. The pH was then adjusted with phosphoric acid and the crosslinking agent added and the mixture vigorously agitated while maintaining the temperature at 60° C.±5° C. The use of the hydrogen peroxide solution as the protein solvent results in the formation of small uniformly dispersed bubbles during the adjustment of the pH addition of the crosslinking agent and thus forms a uniformly porous structure during crosslinking and drying.

In some instances, it may be preferred to freeze-dry the resulting hydrogel-calcium phosphate compositions in lieu of the usual air drying sequences described in prior examples. In any case, the requisite sequence drying initially to a moisture content of not more than 10 percent, preferably 7 percent or less, followed by further soaking in hydrogen peroxide (3% by volume) and organic solvent dehydration as described in Examples 1, 2, and 3, remains desirable in order to obtain bone-like structure having durable wet-strength properties. For example, when placed in water they exhibit a swelling but remain as coherent and do not disintegrate.

These products are new compositions of matter from which useful structures resembling cartilage, bone, and ivory may be produced.

EXAMPLE 9

Fibers, Textile Products, and Sutures

The same composition of water soluble protein hydrogel described for Example 6 is a suitable starting raw material for producing novel fibers capable of being fashioned into many conventional textile forms—webs, fabrics, mats, etc.

The gel, prior to the addition of the crosslinking additive, is pumped into a chamber in sequence with a mechanism capable of extruding the hydrogel through spinnerets to form ultrafine fibers or even monofils; such equipment is commonly used in producing viscose rayons.

The temperature of the gel is kept at 60° C.±5° C. in the antichamber, prior to being passed through a mixing pump into which the appropriate amount of crosslinking agent is metered. The filaments are continuously extruded into long vertical cylindrical drying chambers in which they are dried to a moisture content of not more than 10 percent, preferably 7 percent or less, so that they can be collected on reels or in the form of skeins. Following the initial drying step described above, the yarns are next treated with the same oxidizing treatment (e.g. $H_2O_2$), organic solvent dehydration, extensive final washing, and final drying following the sequence of process steps similar to that described in prior examples.

Such fibers are suitable for a variety of medical and apparel uses. When extruded in the form of small diameter filaments, they may be used as sutures for surgery.

As many apparently widely different embodiments of this invention may be made without departing from the spirit and scope thereof, it is to be understood that I do not limit myself to the specific embodiments thereof except as defined in the following claims:

What is claimed is:

1. The method of preparing a three-dimensional structure comprising forming an aqueous acidic solution of a non-crystalline, natural animal or vegetable protein polymer or mixtures thereof, the polymers having a low molecular weight not exceeding 100,000, heating the solution to a temperature of about 60° C., adding to and incorporating in the solution a crosslinking agent while maintaining the solution at a temperature of about 60° C., drying the solution to a moisture content of not more than 10 percent at a maximum temperature of about 35° C. or equivalent under vacuum to form a crosslinked polymer structure, subjecting the structure to thorough washing with water, subjecting the washed structure to dehydration by immersion in a water-miscible organic solvent, subjecting the structure to thorough washing with water and redrying the dehydrated structure to a moisture content of not more than 10 percent.

2. The method as defined in claim 1 wherein the aqueous acidic solution of the protein polymer has a pH of from about 3.5 to about 5.5.

3. The method as defined in claim 1 wherein the protein polymer is an animal protein.

4. The method as defined in claim 1 wherein the protein polymer is gelatin.

5. The method as defined in claim 1 wherein the protein polymer is a vegetable protein.

6. The method as defined in claim 1 wherein the aqueous acidic solution of the protein polymer is an aqueous hydrochloric acid solution of animal protein having a pH of from about 3.5 to about 5.5.

7. The method as defined in claim 1 wherein the aqueous acidic solution of the protein polymer is an aqueous hydrochloric acid solution of gelatin having a pH of from about 3.5 to about 5.5 and the amount of crosslinking agent is from about 0.5 to about 15 percent based on the weight of gelatin.

8. The method as defined in claim 1 wherein the aqueous acidic solution of the protein polymer is an aqueous hydrochloric acid solution of gelatin having a pH of from about 3.5 to about 5.5 the crosslinking agent is formaldehyde, and the amount of formaldehyde added is from 0.5 to 15 percent, based on the weight of the gelatin.

9. The method as defined in claim 1 wherein after the aqueous acidic solution of the polymer containing the crosslinking agent is dried to form the crosslinked polymer structure, the structure is immersed in an aqueous solution of an oxidizing agent prior to the initial washing with water.

10. The method as defined in claim 1 wherein the water-miscible organic solvent is ethanol.

11. The method as defined in claim 1 wherein the aqueous acidic solution of the protein polymer is an aqueous hydrochloric acid solution of gelatin having a pH of from about 3.5 to 5.5, the crosslinking agent is formaldehyde, the amount of formaldehyde added is from 0.5 to 10 percent, based on the weight of the gelatin, after the solution is dried to form the crosslinked polymer structure, the structure is immersed in an aqueous solution of hydrogen peroxide prior to the initial washing with water and the water-miscible organic solvent is ethanol.

12. The method as defined in claim 1 wherein the aqueous acidic solution of the protein polymer is an aqueous hydrochloric acid solution of an animal protein having a pH of from about 3.5 to about 5.5, a slurry of calcium phosphate is incorporated in the acidic solution prior to the addition of the crosslinking agent, the crosslinking agent is formaldehyde, the amount of formaldehyde added is from about 0.5 to about 15 percent, based on the weight of the animal protein and the water-miscible organic solvent is ethanol.

13. A unitary three-dimensional structure having unique wet-strength properties comprising a cross-linked, non-crystalline natural animal or vegetable protein polymer or mixtures thereof, the polymers having a low molecular weight not exceeding 100,000 and formed by the method as defined in claim 1.

14. A unitary three-dimensional structure as defined in claim 13 wherein the polymer is an animal protein.

15. A unitary three-dimensional structure as defined in claim 13 wherein the polymer is gelatin.

16. A unitary three-dimensional structure as defined in claim 13 wherein the polymer is a vegetable protein.

17. A unitary three-dimensional structure as defined in claim 13 which includes calcium phosphate.

18. A soft contact lens formed by the method of claim 1.

* * * * *